United States Patent [19]

Guerra et al.

[11] Patent Number: 5,527,674
[45] Date of Patent: Jun. 18, 1996

[54] GENETIC CONSTRUCT FOR SELECTION OF HOMOLOGOUS RECOMBINANTS ON A SINGLE SELECTIVE MEDIUM

[75] Inventors: Daniel J. Guerra, Troy; Chengbin Xiang, Moscow, both of Id.

[73] Assignee: Idaho Research Foundation, Inc., Moscow, Id.

[21] Appl. No.: 236,957

[22] Filed: May 2, 1994

Related U.S. Application Data

[63] Continuation of Ser. No. 773,333, Oct. 7, 1991, abandoned.
[51] Int. Cl.$^6$ .......................... C12N 15/82; C12N 15/11; C12Q 1/68
[52] U.S. Cl. ...................... 435/6; 435/69.1; 435/91.1; 435/172.3; 435/240.1; 435/240.4; 435/320.1; 536/23.1; 536/24.5
[58] Field of Search ............................... 435/6, 91.1, 69.1, 435/172.3, 320.1, 240.1, 240.4; 536/23.1, 24.5

[56] References Cited

FOREIGN PATENT DOCUMENTS

| 0240208 | 10/1987 | European Pat. Off. . |
|---|---|---|
| 0335451 | 3/1989 | European Pat. Off. . |
| WO90/08828 | 8/1990 | WIPO . |
| WO91/02070 | 2/1991 | WIPO . |

OTHER PUBLICATIONS

Tomizawa et al., "Inhibition of ColE1 RNA Primer Formation by a Plasmid–Specified Small RNA," *Proc. Natl. Acad. Sci. USA* 78:1421–1425 (1981).
Mizuno et al., "Unique Mechanism Regulating Gene Expression: Translational Inhibition by a Complementary RNA Transcript (micRNA)," *Proc. Natl. Acad. Sci. USA* 81:1966–1970 (1984).
Simons, "Naturally Occurring Antisense RNA Control—A Brief Review," *Gene* 72:35–44 (1988).
Van der Krol et al., "Modulation of Eukaryotic Gene Expression by Complementary RNA or DNA Sequences," *BioTechniques* 6:958–976 (1988a).
Van der Krol et al., "Antisense Genes in Plants: An overview," *Gene* 72:45–50 (1988b).
Izant and Weintraub, "Inhibition of Thymidine Kinase Gene Expression by Anti–Sense RNA: A Molecular Approach to Genetic analysis," *Cell* 36:1007–1015 (1984).
Smith et al., "Antisense RNA Inhibition of Polygalacturonase Gene Expression in Transgenic Tomatoes," *Nature* 334:724–726 (1988).
Sheehy et al., "Reduction of Polygalacturonase Activity in Tomato Fruit by Antisense RNA," Proc. Natl. Acad. Sci. USA85:8805–8809 (1988).
Van der Krol et al., "An Anti–Sense Chalcone Synthase Gene in Transgenic Plants Inhibits Flower Pigmentation," *Nature* 333:866–369 (1988c).
Ecker and Davis, "Inhibition of Gene Expression in Plant Cells by Expression of Antisense RNA," *Proc. Natl. Acad. Sci. USA* 83:5372–5376 (1986).

Rothstein et al., "Stable and Heritable Inhibition of the Expression of Nopaline Synthase in Tobacco Expressing Antisense RNA," *Proc. Natl. Acad. Sci. USA* 84:8439–8443 (1987).
Inouye, "Antisense RNA: Its Functions and Applications in Gene Regulation–A Review," *Gene* 72:25–34 (1988).
Capecchi, "Altering the Genome by Homologous Recomination," *Science* 244:1288–1292 (1989).
Thomas and Capecchi, "Targeting of Genes to Specific Sites in the Mammalian Genome," *Cold Spr. Harb. Symp. Quant. Biol.* 51:1101–1113 (1986).
Thomas and Capecchi, "Site–Directed Mutagensis by Gene Targeting in Mouse Embryo–Derived Stem Cells," *Cell* 51:503–512 (1987).
Smithies et al., "Insertion of DNA Sequences Into the Human Chromosomal β–globin Locus by Homologous Recombination," *Nature* 317:230–234 (1985).
Hinnen et al., "Transformation of Yeast," *Proc. Natl. Acad. Sci. USA* 75:1929–1933 (1978).
DeLozanne and Spudich, "Disruption of the *Dictyostelium myosin* Heavy Chain Gene by homologous Recombination," *Science* 236:1086–1091 (1987).
Lee et al., "Homologous Recombination and Stable Transfection in the Parasitic Protozoan *Trypanosoma brucei,*" *Science* 250:1583–1587 (1991).

(List continued on next page.)

*Primary Examiner*—John L. LeGuyander
*Attorney, Agent, or Firm*—Klarquist Sparkman Campbell Leigh & Whinston

[57] ABSTRACT

Novel genetic constructs and methods for their use in transforming target cells are disclosed. The genetic constructs, which are particularly adapted for homologous recombination with target-cell genomes, comprise a positively selectable genetic marker and a negative selection system "antagonistic" to the expression of the positively selectable marker. The positively selectable marker is situated in a region of the construct between a first and a second flanking sequence homologous to sequences flanking a desired integration site in the target-cell genome. The negative selection system is situated outside the region. The negative selection system preferably comprises an antisense gene that prevents expression of the positively selectable marker. The positively selectable marker preferably encodes an antibiotic resistance factor. The construct can also include a "gene of interest", also situated between the homologous flanking sequences adjacent the positively selectable marker, for introduction via homologous recombination into the target genome at the desired integration site. Transformed target cells whose genomes homologously recombine with the genetic construct acquire the positively selectable marker and (if present) the gene of interest. Non-homologous recombinants acquire both the positively selectable marker and the negative selection system, thereby losing the ability to survive exposure to the corresponding positive selection agent. Non-recombinants acquire no part of the construct. Thus, homologous recombinants have the exclusive ability to survive exposure to the positive selection agent and can be easily isolated from all other target cells.

21 Claims, 2 Drawing Sheets

OTHER PUBLICATIONS

Horng et al., "Development of a Homologous Transformation System for *Aspergillus parasiticus* with the Gene Encoding Nitrate Reductase," *Mol. Gen. Genet.* 224:294–296 (1990).

Gal et al., "Genomic Homologous Recombination in Planta," *Embo J.* 10:1571–1578 (1991).

Wong and Capecchi, "Homologous Recombination Between Coinjected DNa Sequences Peaks in Early to Mid–S Phase," *Molec. Cell. Biol.* 7:2294–2295 (1987).

Toulmé and Hélène, "Antimessenger Oligodeoxyribonucleotides: An Alternative to Antisense RNA for Artificial Regulation of Gene Expression—A Review," *Gene* 72:51–58 (1988).

Rothstein et al., "Silencing Gene Expression in Plants," In *Oxford Surveys of Plant Mol. & Cell Biol.* 6:221–246 (1989).

GENETIC CONSTRUCT FOR SELECTION OF HOMOLOGOUS RECOMBINANTS ON A SINGLE SELECTIVE MEDIUM

This is a continuation of application Ser. No. 07/773,333, filed Oct. 7, 1991, now abandoned.

FIELD OF THE INVENTION

This invention pertains to the fields of recombinant DNA technology, transformation of cells, and genetic selection of transformed cells.

BACKGROUND OF THE INVENTION

Gene Regulation by Antisense

A principal scheme by which information is transferred from a gene is, first, by transcription of the gene to form a corresponding RNA message ("messenger RNA" or "mRNA"), then by translation of the mRNA to form a corresponding protein. This seemingly simple scheme is effected by complex mechanisms in living cells. This scheme is further complicated by the fact that not all genes in a cell's genome are expressed at the same time. Cells possess complex gene regulatory mechanisms that selectively turn genes on and off, thereby determining cell structure, function, and developmental fate.

Certain classes of genes in cells are termed "regulatory genes" because they regulate the expression of other genes. One class is comprised of regulatory genes encoding regulator proteins that interact with other specific genes at the transcriptional or translational level to modulate the amount of protein produced by the regulated gene, often in response to environmental cues. Other classes of regulatory genes function by means other than by producing a regulatory protein.

Mounting evidence indicates that an important naturally occurring means of gene regulation is by "antisense" transcripts, particularly in procaryotic cells. Tomizawa et al., *Proc. Natl. Acad. Sci. USA* 78:1421–1425 (1981); Mizuno et al., *Proc. Natl. Acad. Sci. USA* 81:1966–1970 (1984); Simons, *Gene* 72:35–44 (1988). (Although RNAs from eucaryotic cells have been found that are complementary to known genes, an in vivo regulatory role of these RNAs has not been proven. Van der Krol et al., *Biotechniques* 6:958–976 (1988)). An antisense transcript, termed "antisense RNA", is comprised of a nucleotide sequence complementary to either an mRNA encoded by a regulated gene or to the "sense strand" of DNA comprising the regulated gene. One probable mechanism by which an antisense RNA regulates a gene is by the formation of a hybrid RNA duplex of the antisense RNA with a particular mRNA via Watson-Crick base pairing. Van der Krol et al., *Gene* 72:45–50 (1988). Such hybrids appear to be resistant to translation for any of a number of reasons including unusually rapid degradation of the duplex in the cell, impairment of post-transcriptional processing, or inhibition of ribosome binding. Simons, *Gene* 72:35–44 (1988); Van der Krol et al., *Gene* 72:45–50 (1988). Genes that encode antisense RNAs are termed "antisense genes".

After the discovery of antisense RNAs, researchers began investigating ways to artificially regulate gene expression using antisense RNAs. These studies have proven effective in identifying specific genes, characterizing gene function, controlling infections, and manipulating metabolic pathways. Van der Krol et al., *BioTechniques* 6:958–976 (1988). For example, antisense RNA synthesized in vitro and introduced into eucaryotic cells can regulate expression of specific genes within the cells, at least temporarily. Izant and Weintraub, *Cell* 36:1007–1015 (1984); Izant and Weintraub, *Science* 229:345–352 (1985); Van der Krol et al., *BioTechniques* 6:958–976 (1988). These experiments have not only been performed using mammalian cells but also plant cells. Van der Krol et al., *Gene* 72:45–50 (1988); Smith et al., *Nature* 334:724–726 (1988); Sheehy et al., *Proc. Natl. Acad. Sci, USA* 85:8805–8809 (1988); Van der Krol et al., *Nature* 333:866–869 (1988); Ecker et al., *Proc. Natl. Acad. Sci. USA* 83:5372–5376 (1986); and Rothstein et al., *Proc, Natl. Acad. Sci. USA* 84:8439–8443 (1987). simultaneous development of gene sequencing, gene cloning, and in vitro gene and RNA synthesis technology made it possible to readily generate antisense RNAs to target genes, provided the target gene or the nucleotide sequence of the target gene was available. Inouye, *Gene* 72:25–34 (1988).

Antisense RNA can be used to mimic mutations in both procaryotic and eucaryotic organisms. Takayama and Inouye, *Crit. Rev. in Biochem. and Molec, Biol.*, CRC Press 25:155–184 (1990); van der Krol et al., *BioTechniques* 958–976 (1987). In plants, antisense RNA has been successfully used to inhibit the activity of nopaline synthase, Rothstein et al., *Proc. Natl. Acad. Sci. USA* 84:8439–8443 (1987); Sandler et al., *Plant Mol. Biol.* 11:301–310 (1988); chloramphenicol acetyltransferase, Ecker and Davis, *Proc. Natl. Acad. Sci, USA* 83:5372–5376 (1986); Delauney et al., *Proc. Natl. Acad. Sci. USA* 85:4300–4304 (1900); chalcone synthase, van der Krol et al., *Nature* 333:866–869 (1988); polygalacturonase, Smith et al., *Nature* 334:724–726 (1988); Sheehy et al., *Proc. Natl. Acad. Sci. USA* 85:8805–8809 (1988); β-glucuronidase, Robert et al., *Plant Mol. Biol.* 13:399–409 (1989); and granule-bound starch synthase, Visser et al., *Mol. Gen. Genet.* 225:289–296 (1991).

Because mRNAs have only a limited life in cells, antisense RNA injected into cells generally exhibits a regulatory function of relatively short duration. However, functional antisense genes can be made in vitro by coupling a functional promoter to a DNA sequence oriented in a way wherein the promoter induces transcription of the noncoding (or "nonsense") strand of the DNA, rather than the normal coding (or "sense") strand. One approach is to invert the coding sequence of the DNA relative to the promoter. Izant and Weintraub, *Science* 229:345–352 (1985). This can be done by excising the coding region of the gene, proximal to the promoter and polyadenylation sites, and reinserting the excised portion in reverse orientation relative to the promoter. Izant and Weintraub, *Cell* 36:1007–1015 (1984). Thus, the antisense gene is transcribed in a direction opposite to the direction of transcription of the corresponding sense gene. Mizuno et al., *Proc. Natl Acad. Sci USA* 81:1966–1970 (1984). When such an antisense gene is introduced into a recipient cell having an endogenous corresponding "sense" gene, the promoter directs transcription of the nonsense DNA strand, producing a transcript (antisense RNA) complementary to mRNAs normally produced by the corresponding "sense" gene. Introduction of an antisense gene into a cell has been found to result in a more prolonged, or stable, regulatory effect than introduction of antisense RNA, so long as the introduced antisense gene continues to be transcribed by the cell. Of course, integrating the introduced antisense gene into the cell genome can result in continued expression of the antisense gene over the lifetime of the cell.

Many plant cells, in contrast to the vast majority of other eucaryotic cells, are totipotent. That is, individual totipotent plant cells can be readily induced to divide and form entire plants. Hence, introduction of an exogenous antisense regulatory gene into a totipotent plant cell, wherein the antisense gene integrates into the cellular genome, can yield a source of "genetically engineered" plants expressing the new antisense gene in their cells and passing the antisense gene to their progeny. Rothstein et al., *Proc. Natl. Acad. Sci. USA* 84:8439–8443 (1987).

Homologous Recombination

When an exogenous gene is introduced into a cell, the introduced gene can become integrated into the cell genome. Random integrations are very inefficient in producing specific desired genetic alterations. However, it is now possible to "target" the integration to a specific site in the cell genome by a technique known as homologous recombination. See, e.g., Capecchi, *Trends Genet.* 5:70–76 (1989); Capecchi, *Science* 224:1288–1292 (1989).

Homologous recombination has been utilized for insertion of exogenous and other genetic sequences into cellular genomes, for replacement of endogenous genome sequences with introduced sequences, and for inducing mutations in a particular endogenous gene by "heteroduplex-induced mutagenesis" resulting from incorrect repair of a transient heteroduplex that forms between the newly introduced DNA and the homologous chromosomal sequence during the homologous recombination event. Thomas and Capecchi, *Cold Spring Harbor Symp. on Quant. Biol.* 51:1101–1113 (1986); Thomas and Capecchi, *Cell* 51:503–512 (1987).

When homologous recombination results in insertion of the introduced DNA sequence into the cell genome, the inserted DNA is placed under normal endogenous controls by which expression of genes is regulated in the cell. Thus, the introduced gene can be employed to repair a genetic lesion in the cell, impart a modified phenotype to the cell, or disrupt a preexisting allele in the cell. For example, gene targeting via homologous recombination was employed to create a large deletion at the T-cell antigen receptor S-subunit locus in mouse embryo stem cells, Mombaerts et al., *Proc. Natl. Acad. Sci. USA* 88:3084–3087 (1991); and a subtle mutation was introduced into the hox-2.6 locus in embryo stem cells, Hasty et al., *Nature* 350:243–246 (1991). Besides mouse cells, Chisaka et al., *Nature* 350:473–479 (1991), gene targeting has been described in other eucaryotic systems including human cells, Smithies et al., *Nature* 317:230–234 (1985); yeast, Hinnen et al., *Proc. Natl. Acad. Sci. USA* 75:1929–1933 (1978); *Dictyostelium*, De Lozanne et al., *Science* 236:1086–1091 (1987); *Trypanosoma brucei*, Lee et al., *Science* 250:1583–1587 (1991); and *Aspergillus parasiticus*, Horng et al., *Mol. Gen. Genet.* 4:294–296 (1990).

Gene targeting has also been utilized in plants. Gal et al., *EMBO J.* 10:1571–1578 (1991); Pazkowski et al., *EMBO J.* 7:4021–4026 (1988); Offringa et al., *EMBO J.* 9:3077–3084 (1990); Peterhaus et al., *EMBO J.* 9:3437–3445 (1990); and Lee et al., *Plant Cell* 2:415–425 (1990). In this work, defective selectable marker genes were stably integrated into the nuclear genomes of subject plant cells by using either direct (e.g., via electroporation or microinjection) or *Agrobacterium*-mediated gene transfer. Subsequently, "correct" exogenous DNA sequences were introduced into the plant cells harboring the previously introduced defective markers, resulting in a restored selectable marker via homologous recombination.

Gene targeting requires that a highly discriminating procedure be utilized to isolate cells that have undergone the desired homologous recombination. The frequency of transgene homologous recombination is reportedly about one in $10^3$ to about one in $10^5$. Lee et al., *Plant Cell* 2:415–425 (1990). All gene targeting experiments performed to date with higher plants, including experiments reported in the references cited in the previous paragraph, involved the introduction into subject plant cells of positively-selectable marker genes. While these experiments demonstrated that gene targeting in higher plants was possible, they also showed that, even with positively-selectable markers, exhaustive screening techniques such as Southern blotting were required in order to distinguish and isolate the relatively very few homologously recombinant cells that were formed from other recombinants and from non-recombinants. Capecchi, *Science* 244:1288–1293 (1989). The experiments also indicated that gene targeting in plants, using existing methods, could not be readily performed at all using nonselectable genes or DNA sequences that do not possess a selectable marker. In addition, there are no practical or reliable negatively selectable markers for plant systems. These problems pose a major barrier for the application of gene targeting in higher plants.

As with plant cells, there is also a need for a practical way to distinguish and isolate homologously recombinant animal cells from a population comprised of homologous recombinants, non-homologous recombinants, and non-recombinants. Existing methods for animal cells are difficult, time-consuming, and/or expensive to perform, requiring either multiple selection agents and/or exhaustive screening of the entire population of cells.

Hence, there is a need for a practical way, after introducing genetic constructs into cells to undergo homologous recombination with the cellular genomes, for identifying and isolating the desired homologous recombinants from the entire population of transformed and non-transformed cells.

There is also a need for genetic constructs capable of undergoing homologous recombination with the genomes of target cells which confer upon the resulting homologous recombinants the ability to be selected for using only one positive selection agent, thereby permitting the desired homologous recombinants to be readily recovered from other cells that are either non-transformed or non-homologously transformed.

SUMMARY OF THE INVENTION

The aforementioned needs are met by the present invention which provides genetic constructs capable of homologous recombination with an integration site in the genomic DNA of target cells. The genetic constructs are particularly adapted for introducing new genetic information or mutations at specific site(s) in the genomes of target cells while enabling only those target cells that have acquired the new information or mutation at the desired site(s) to be readily isolated from all other cells. Thus, expensive and time-consuming screening procedures are obviated because the previously mandatory need to screen all the target cells is eliminated.

A genetic construct according to the present invention comprises a positively selectable genetic marker that integrates into the genomic DNA at the integration site during recombination events between the construct and the genomic DNA. The genetic construct also comprises a negative selection system "antagonistic" to expression of the positively selectable genetic marker. The negative selection system is integratable into the genomic DNA via non-homologous recombination between the construct and the genomic DNA but not via homologous recombination.

Genetic constructs according to the present invention confer only upon homologously recombinant cells the ability to survive exposure to a single positive selection agent (to which the positively selectable genetic marker confers resistance); non-recombinants and non-homologous recombinants are incapable of surviving exposure to the positive selection agent.

The positively selectable genetic marker preferably, but not necessarily, encodes an antibiotic resistance factor. The negative selection system is preferably comprised of an antisense gene of the positively selectable marker. Thus, for example, in non-homologous recombinants receiving both the gene encoding the antibiotic resistance factor and the antisense gene, the antisense gene blocks expression of the antibiotic resistance gene, rendering the non-homologous recombinant target cell incapable of surviving exposure to the corresponding antibiotic. Also, since non-recombinants never acquire the antibiotic-resistance gene, they are also killed by the antibiotic. Homologous recombinants, on the other hand, integrate the gene for antibiotic resistance but do not integrate the antisense gene. Therefore, homologous recombinants are the only cells that survive exposure to the antibiotic.

Selective integration of the positively selectable genetic marker (but not the negative selection system) at the desired site in the target cell genome is made possible by placing the positively selectable marker inside a region bounded by flanking sequences homologous to genetic sequences flanking the desired integration site in the target cell genome. The negative selection system, however, is located outside the region bounded by the homologous flanking sequences. Thus, the negative selection system is not integrated into the target cell genome via a homologous recombination event.

Genetic constructs according to the present invention can also include a "gene of interest" adjacent the positively selectable marker gene between the homologous flanking sequences. Target cells into which such a construct is introduced will integrate not only the positively selectable marker but also the gene of interest as a result of a homologous recombination event. The gene of interest can be an "improved" gene from the target-cell organism, a gene from a different type of organism, a group of genes, or portion of a gene or genes. Thus, it is now possible to introduce specific genetic changes at specific genomic sites in target cells without having to laboriously screen all target cells for "proper" recombinants.

If the target cells have totipotency, it is now also possible to impart desired genetic changes in such target cells, rapidly and inexpensively screen the putative homologous recombinants, and generate genetically identical entire organisms from the "proper" recombinants. Because many plant cells are totipotent and can be readily induced to develop into new plants, the present invention has unlimited benefit in the "genetic engineering" of improved varieties of plants.

A general requirement of the target cells is that they be able to express the genetic information supplied to the cells in the genetic constructs of the present invention. Thus, if the negative selection system comprises an antisense gene to the positively selectable marker gene, it is necessary that the target cell be able to express the antisense gene. Accordingly, the positively selectable marker gene and the negative selection gene must each be in the proper "sense" and be controlled by a promoter and a terminator expressible in the target cells.

The genetic constructs according to the present invention can be constructed using any of the well-developed methods used in the art for rearranging, cloning, and assaying new genetic constructs. Likewise, they can be introduced into target cells by any of a variety of methods known in the art, including using a vector delivered by an infectious agent, electroporation, or other technique.

DETAILED DESCRIPTION

According to one aspect of the present invention, gene constructs are provided that, in general, are capable of homologous recombination with genomic DNA of target cells so as to introduce new DNA sequences into the cells' genomic DNA. Such gene constructs are referred to as being capable of "transforming" target cells of interest. (As used herein, "transformation" is a process by which naked DNA is introduced into a cell so as to cause a heritable change to the cell.) The gene constructs have particular utility for use in transforming cells by homologous recombination, wherein it is desired that only homologous recombinants, not non-homologous recombinants or non-recombinants, be recovered. The present invention makes it possible, for the first time, to recover homologous recombinants by a simple, easy, and inexpensive selection procedure requiring only a single selective medium.

Figure 1:
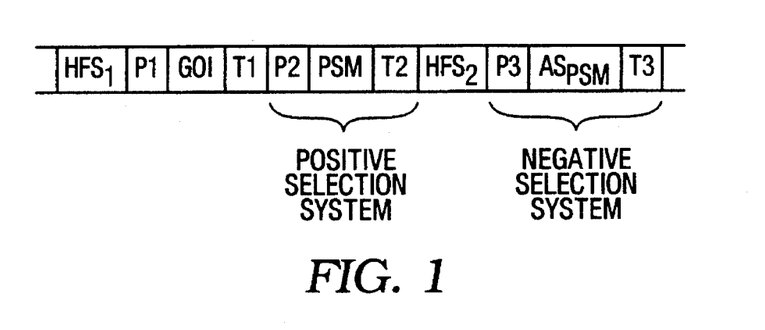
FIG. 1 shows a generic scheme of a genetic construct according to the present invention.

Each gene construct, as shown generally in FIG. 1, comprises both a positive selection system and a negative selection system. The positive selection system comprises a positively selectable marker (PSM) locus such as, but not limited to, a locus encoding an antibiotic resistance factor. The negative selection system comprises a locus "antagonistic" to the PSM locus, i.e., the negative selection system blocks expression of the PSM locus. A preferred type of negative selection system comprises an "antisense locus" ($AS_{PSM}$ locus) encoding an antisense RNA capable of blocking expression of the PSM locus.

The $AS_{PSM}$ locus exercises its blocking function against the PSM locus by any of several antisense mechanisms known in the art, including inhibition of transcription (e.g., by binding to DNA encoding the PSM locus), by binding to mRNA transcribed from the PSM locus before the mRNA is translated, or by otherwise interfering with the translation machinery in the target cell (e.g., binding to ribosomes). The present state of knowledge pertaining to antisense action indicates that inhibition of translation is the predominant general mechanism of antisense RNA action.

Optionally included in the gene construct is a "gene of interest" (GOI) locus encoding one or more genes (which can be non-selectable genes), or a portion of a gene, intended to be incorporated by homologous recombination into the genomes of recipient, or "target", cells. If present, the GOI locus is situated adjacent the PSM locus.

The PSM locus, and the GOI locus if present, are situated between homologous genomic flanking sequences designated "HFS$_1$" and "HFS$_2$" in FIG. 1. The HFS$_1$ and HFS$_2$ sequences are homologous to genomic sequences normally flanking the 5' and 3' ends of a desired integration site in the cell genome. For example, if the desired integration site is a particular gene, the HFS$_1$ and HFS$_2$ sequences are homologous to genomic sequences flanking that gene in the target cell genome. As has been established in the research literature, homologous flanking sequences on a length of DNA introduced into a cell to transform the cell substantially increase the probability that the DNA extending between the homologous flanking sequences will integrate at the desired site in the target cell genome. Thomas and Capecchi, *Cold Spr. Harb. Symp. Quant. Biol.* 51:1101–1113 (1986).

As shown in FIG. 1, the AS$_{PSM}$ locus is situated on the construct outside the region flanked by HFS$_1$ and HFS$_2$. This ensures that the AS$_{PSM}$ locus will not become integrated into the target cell genome as a result of a desired homologous recombination event, but will likely become integrated if the construct integrates into the target genome via non-homologous recombination. Non-recombinants acquire neither the PSM locus nor the AS$_{PSM}$ locus. Thus, homologous recombinants acquire the PSM locus conferring an ability to survive in a single selective medium but do not acquire the AS$_{PSM}$ locus antagonistic to expression of the PSM locus. Since non-homologous recombinants acquire both loci, they lack an ability to survive in the single selective medium. Because non-recombinants acquire neither locus, they also lack an ability to survive in the single selective medium. As a result, only homologous recombinants survive.

If the GOI locus comprises an entire gene intended to be introduced into a target cell to replace a corresponding defective gene in the cell genome, the HFSs are preferably homologous to sequences present on each side of the defective gene in the cell genome. If the GOI comprises only a portion of a gene, the HFSs can be homologous to other portions of the same gene adjacent the portion of the gene comprising the GOI.

The GOI locus (if present), PSM locus, and AS$_{PSM}$ locus must be present in the gene construct in the proper sense. In addition, the PSM and AS$_{PSM}$ loci, and usually the GOI locus (if present) must be served by a suitable transcription promoter, designated in FIG. 1 as P1, P2, and P3, respectively. (As used herein, a "suitable" promoter is one that will function in the target cell and that will promote transcription of the corresponding locus.) But, the promoters need not be different; for example, the GOI and PSM loci can be controlled by the same promoter (i.e., P1 and P2 need not be different promoters). In addition, the PSM and AS$_{PSM}$ loci, and usually the GOI locus (if present), must include a suitable transcription terminator, designated in FIG. 1 as T1, T2, and T3, respectively. If the GOI locus is only a portion of a complete gene of interest and is intended to impart a localized mutation to a gene in the target cell genome, there may be instances in which it is not necessary for the GOI to have a promoter or terminator.

It is preferred that P3, the antisense promoter, be a stronger promoter than P2, the PSM promoter, for effective inhibition of PSM expression by AS$_{PSM}$ transcripts. See, van der Krol et al., *Nature* 333:866–869 (1988). A strong P3 ensures a high production of antisense RNA relative to PSM transcripts. This is important because previous work has shown that there is a gene dosage effect of antisense RNA regulation. Inouye, *Gene* 72:25–44 (1988). Alternatively, an increase in antisense RNA production, relative to PSM production, can be achieved by incorporating into the construct of FIG. 1 multiple copies of AS$_{PSM}$. Id.

The following are representative examples of suitable promoters for gene constructs according to the present invention. These examples, however, are not in any way intended to be limiting because the research literature has many representative examples of promoters that could be used and that are well within the skill of practicing artisans to utilize in assembling a gene construct according to the present invention. One example of a suitable PSM promoter (P2) is the relatively weak NOS (hopaline synthase) promoter; a strong antisense promoter (especially relative to the NOS promoter and particularly adapted for gene constructs intended for transforming plant cells) is the 35S promoter from cauliflower mosaic virus (CaMV). The 35S promoter has the additional benefit of being a "constitutive" promoter, meaning that it is expressible in a wide variety of systems. An alternative AS promoter is the moderately strong PAL gene promoter. Other promoters include the "rubisco" promoter, the chlorophyll AB binding protein (CAB) promoter, and heat-shock promoters. A rule of thumb to keep in mind is that the AS promoter should be stronger than the PSM promoter to ensure relatively high expression of the antisense RNA.

Under certain instances, it is advantageous to use regulable promoters, particularly if it is important to be able to turn expression of the corresponding gene on and off or to modulate expression of the gene at will. Examples of regulable promoters include, but are not limited to, inducible promoters (such as heat-shock promoters), repressible promoters, polymerase-specific promoters, development-specific promoters, and tissue-specific promoters.

As stated above, the GOI can comprise a single gene, plural genes, or one or more portions of a gene or genes. For example, the GOI can comprise an entire structural gene (such as a gene encoding a novel enzyme) not normally present or expressed in the target cells. As further examples, and in accordance with a voluminous research literature showing the introduction of a wide variety of "foreign" genes into cells, the GOI can comprise a procaryotic structural gene to be transferred into plant cells or a plant gene to be transferred into mammalian cells or a mammalian gene to be transferred into plant cells. Alternatively, the GOI can comprise a portion of a gene, in which instance the construct that includes the gene portion can be used to impart site-specific mutagenesis of a corresponding gene in the target-cell genome. In fact, such a gene portion can be as small as a single nucleotide.

The target cells can be plant cells or animal cells. In fact, there is no known limit to the types of target cells transformable by genetic constructs according to the present invention. This is further evidenced by the fact that, as supported by a voluminous research literature, artificially introduced "foreign" antisense genes can function in a wide variety of recipient cell types. Therefore, it can be stated with confidence that constructs according to the present invention containing an AS$_{PSM}$ locus will function in any recipient cell capable of expressing antisense genes. In addition, the method by which the constructs are delivered inside the target cells can be any of the several methods known in the art including, but not limited to, delivery by an infectious-agent vector (such as by Agrobacterium infection of target plant cells), electroporation, particle-gun bombardment, and other suitable methods.

Depending upon the transformation method and the type of target cell, genetic constructs according to the present invention can have additional features. To illustrate, if the construct is used to transform plant cells, it can include features normally found on plasmids conventionally used to transform plant cells. For example, transformation of plant cells is commonly performed using a plasmid vector derived from T-DNA (virulence plasmid) of *Agrobacterium tumefaciens*. These plasmids include "right border" (RB) and "left border" (LB) regions that facilitate transformation; that is, the RB and LB regions increase the frequency of transformation of the target plant cells. It will be appreciated that, if the construct is used to transform animal cells, RB and LB regions are not necessary and can be, if desired, replaced with other regions that enhance transformation of animal cells.

A gene construct according to the present invention is constructed by techniques within the knowledge and experience of persons skilled in the art. That is, the methodology of constructing in vitro novel combinations of genetic elements is well within the purview of persons skilled in the art armed with an arsenal of restriction enzymes and familiar with gene cloning techniques. These techniques are extensively detailed, for example, in Sambrook et al., *Molecular Cloning, A Laboratory Manual*, 2d ed. (3 volumes), Cold Spring Harbor Laboratory (1989). Hence, it will be appreciated that the PSM locus can comprise any of a variety of known clonable positive selectable markers, such as any of various antibiotic resistance markers described in the literature. Likewise, the GOI can be virtually any gene or gene fragment of interest, including any of the thousands described in the research literature. Since the PSM locus is clonable, it is a routine matter to generate an antisense locus corresponding to the PSM locus. Inouye, *Gene* 72:25-34 (1988). Linking of the elements comprising a genetic construct according to the present invention is also within the purview of persons skilled in the art, employing the standard arsenal of restriction enzymes and using conventional separation and assay techniques.

Selecting proper $HFS_1$ and $HFS_2$ loci to include in a gene construct according to the present invention is also within the purview of persons skilled in the art. Typically, molecular genetic details of the GOI will be known, including restriction enzyme cleavage maps and even an actual sequence of the GOI together with flanking sequences. (Knowledge of the actual nucleotide sequence of the GOI and flanking sequences is not required if suitable restriction fragments are available.)

The length of the $HFS_1$ and $HFS_2$ loci can vary. It will be appreciated by persons skilled in the art that increasing the length of the HFSs (within certain limits) will correspondingly improve the likelihood that the gene construct will "find" the desired integration site in the target cell genome and successfully undergo recombination at that site. That is, increasing the length of the HFSs can yield a corresponding increase in the efficiency of successful recombination. Based on homologous recombination studies reported in the research literature performed using mammalian cells, and on our own research, an effective lower limit of the combined length of $HFS_1$ and $HFS_2$ is about 0.2 kilobases (kb). A reasonable upper limit is about 4.0 kb. The preferred range is between about 2.0 kb and 4.0 kb. It will also be appreciated that the total HFS length may have to be limited due to practical upper limits on the size of the gene construct according to the present invention that can be delivered into a particular type of cell undergoing transformation. That is, the lengths of the GOI, PSM, $AS_{PSM}$, and other loci on the construct, relative to the maximal allowable length of the construct, may demand that the HFSs be shorter than optimal.

The length of the $AS_{PSM}$ locus will depend in part upon the length of the PSM. However, the $AS_{PSM}$ locus need not be so long as to produce an antisense RNA having the same length as the PSM transcript. The length of the $AS_{PSM}$ locus will also depend in part upon the mechanism of inhibitory action of the particular antisense RNA encoded by the $AS_{PSM}$ locus selected; e.g., whether the antisense RNA acts by binding directly to coding regions of PSM mRNA so as to directly inhibit translation of the mRNA, whether the antisense RNA acts by binding to noncoding regions of PSM mRNA so as to inhibit translation, or whether the antisense RNA interferes in some way at the transcriptional level. A longer antisense RNA is not necessarily better than a short antisense RNA. For example, in eucaryotes, sense-antisense hybrid formation at the 5'-end non-coding region of an mRNA can be more effective than such a hybrid encompassing the entire coding region. Inouye, *Gene* 72:25-44 (1988). An antisense RNA that binds solely to the translation initiation site on the target mRNA can be effective, even though such an antisense RNA is typically very short, only a few nucleotides long. Simons, *Gene* 72:35-44 (1988). In short, it is well within the purview of a person skilled in the art to design a suitable $AS_{PSM}$ locus, based upon a knowledge of the PSM gene selected for use in the gene construct and upon general principles of antisense RNA action as discussed in a number of reviews on the subject. See, e.g., Simons, id.; Inouye, *Gene* 72:25-44 (1988); and van der Krol et al., *Gene* 72:45-50 (1988).

Basically, the positive selection system works as follows: Transformant target cells that have integrated the PSM locus into their genomes will be capable of surviving in an environment selective against cells lacking the PSM locus. That is, transformants possessing a functional and unblocked PSM locus will be positively selected for when cultured in a selective medium. As stated above, a particularly suitable PSM locus encodes an antibiotic resistance factor that confers upon cells possessing the locus the ability to survive in a culture medium containing the corresponding antibiotic. Any cell lacking an antibiotic-resistance PSM locus, or in which the PSM locus is present but expression thereof is somehow blocked or inhibited, will be killed in medium containing the antibiotic.

The negative selection system works as follows: Transformant cells that have integrated both the PSM and AS loci into their genomes (by non-homologous recombination) will produce antisense RNA that blocks expression of the PSM locus. As a result, the transformants will not produce the corresponding PSM-encoded factor (such as an antibiotic resistance factor) that would otherwise enable the cell to survive in a selective medium. That is, cells possessing the $AS_{PSM}$ and PSM loci (or just the $AS_{PSM}$ locus) are negatively selected against when incubated in selective medium (such as a medium containing the corresponding antibiotic).

As can be seen, both the PSM and $AS_{PSM}$ loci are required in the construct. If the construct lacked the $AS_{PSM}$ locus, then all cells incorporating the construct would be resistant to the antibiotic and would survive. But, there would be no way to selectively distinguish cells that had undergone homologous recombination from cells that had incorporated the construct via non-homologous recombination. The $AS_{PSM}$ locus located outside the region bounded by $HFS_1$ and $HFS_2$ provides the necessary negative selection against non-homologous recombinants. This is because homologous recombination of the gene construct with the genome of the target cell occurs at $HFS_1$ and $HFS_2$. Any portions of the gene construct located outside the region between $HFS_1$ and $HFS_2$ are not incorporated into the target cell genome during homologous recombination and are rapidly degraded. Therefore, in order for the $AS_{PSM}$ locus to negatively select against non-homologous transformants, it must be located outside the region between $HFS_1$ and $HFS_2$.

It should be kept in mind that transformed cells that survive incubation in the positive-selection medium (e.g, containing antibiotic) are regarded as "putative recombinants". The surviving subpopulation of putative recombinants must still be screened using conventional techniques (such as Southern blotting) to identify actual (or the best) recombinants. A key advantage of the present invention is that it obviates, for the first time, the necessity to screen the entire population of transformed cells. This is because non-homologously transformed and non-transformed cells (which are not wanted anyway and which represent the majority of the cells) will not survive the positive selection. Thus, the expensive and time-consuming task of screening cells is greatly reduced, at least by several orders of magnitude.

Embodiments Adaptable for Transforming Plant Cells

Gene constructs as described hereinbelow are particularly adapted to be introduced into plant cells using known plant-cell transformation techniques. The availability of gene constructs according to the present invention for introduction into plant cells represents a substantial advance because, without exception, all gene targeting experiments performed to date in higher plants exploited positive selectable marker genes that required exhaustive screening techniques including Southern blotting of all recombinants. Also, there are currently no universally reliable negatively selectable markers available for plant systems. Constructs according to the present invention make it possible, for the first time, to perform targeting of virtually any gene into plant cells and to readily, conveniently, and inexpensively select for the desired recombinants.

Candidate transformation techniques utilizable with constructs according to the present invention are well known in the art. These include, but are not limited to, utilization of *Agrobacterium tumefaciens* T-DNA as a vector, electroporation, and particle-gun ("gene gun") bombardment of recipient cells. Use of T-DNA as a vector is a well-known and widely utilized and highly efficient method for delivering DNA into plant cells obtained from dicotyledonous plants. Electroporation and gene gun techniques are more suitable for monocotyledonous plant cells (such as cells from grasses) with which T-DNA is either ineffective or greatly inefficient. However, electroporation and gene gun techniques are less efficient in causing actual integration of the introduced DNA into the target cell genome.

In general, an embodiment of a construct adaptable for transforming plant cells is constructed and works as follows: In the construct, an antibiotic-resistance PSM gene is placed between suitable $HFS_1$ and $HFS_2$ loci and an antisense gene to the PSM is placed outside the region bounded by $HFS_1$ and $HFS_2$. A GOI, if desired, is coupled to the PSM locus between $HFS_1$ and $HFS_2$. Each of the PSM, GOI (if present), and $AS_{PSM}$ loci are governed by suitable promoters and terminators included in the gene construct as shown generally in FIG. 1. The construct is administered to target plant cells via a suitable transformation procedure such as Agrobacterium infection. The cells are then cultured in a medium containing the antibiotic. Cells in which a random integration or non-homologous recombination event occurred involving the construct are sensitive to the antibiotic because the antisense gene will block PSM expression. Cells in which a homologous recombination event occurred are resistant to the antibiotic because only the antibiotic-resistance factor coded by PSM, not additionally the antisense gene, was integrated into the cell genome. Thus, a single positive selection agent (the antibiotic) is used to obtain a vastly enriched subpopulation, relative to the population of all target cells, of transformed plant cells that underwent homologous recombination at the desired site or sites in the target cell genome.

Figure 2:
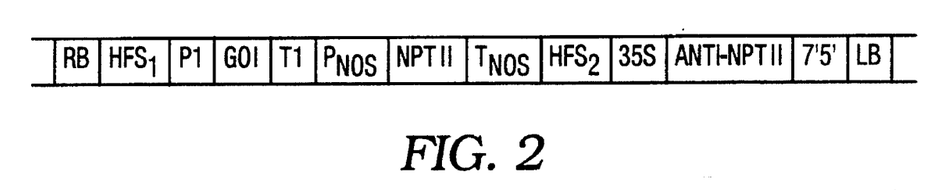
FIG. 2 is a representative embodiment of the construct of FIG. 1 particularly suitable for transforming plant cells.

By way of example, and not intended to be in any way limiting, one possible general embodiment of a construct suitable for transforming plant cells is shown schematically in FIG. 2. The FIG. 2 construct is inherently capable of integrating any of a wide variety of genes of interest (GOI) into dicotyledonous plant cells at predetermined integration sites in the cell genomes. Homologous recombinants resulting from such integration can be readily selected using a single positive selection agent from a large population of cells receiving the construct. The FIG. 2 construct possesses general features of such constructs according to the present invention: (a) a positively-selectable marker gene such as the NPTII gene encoding neomycin phosphotransferase conferring ability to grow in the presence of kanamycin (the arrow indicates the sense direction); (b) homologous genomic flanking sequences ($HFS_1$ and $HFS_2$) having a region therebetween comprising the marker gene (NPTII), wherein $HFS_1$ and $HFS_2$ serve to "target" the gene construct to integrate at a desired site or sites in the cell genome via homologous recombination; (c) an optional gene of interest (GOI) located adjacent the marker gene and between $HFS_1$ and $HFS_2$, the GOI intended to be integrated into the cell genome at the target site; (d) an antisense gene to the positively selectable marker gene (the antisense gene designated in FIG. 2 as "Anti-NPTII") situated outside the region bounded by $HFS_1$ and $HFS_2$; (e) a functional promoter for each of the GOI (if present), NPTII, and Anti-NPTII loci (P1, $P_{NOS}$, and 35S, respectively); and (f) a functional terminator for each of the GOI (if present), NPTII, and Anti-NPTII loci (T1, $T_{NOS}$, and 7'5', respectively, wherein the 7'5 'terminator is a strong Agrobacterium terminator known in the art).

The FIG. 2 construct is designed to utilize *Agrobacterium tumefaciens* T-DNA as a vector. T-DNA is a circular duplex DNA "virulence" plasmid of *A. tumefaciens*. T-DNA comprises an "RB" (right boundary) locus on one end and a "LB" (left boundary) locus on the opposing end. Published research indicates that the RB and LB loci facilitate integration of T-DNA at various locations in the plant-cell genome and thereby greatly improve the efficiency of plant-cell transformation.

If T-DNA is the vector as shown in FIG. 2, it is apparently necessary that $HFS_1$ be adjacent the RB locus rather than the LB locus to ensure efficient transformation.

If the plant cells to be transformed are obtained from monocots rather than dicots, use of *A. tumefaciens* T-DNA is generally not indicated because this bacterium does not efficiently transform monocotyledonous plants. Thus, a gene construct according to the present invention for use in monocot target cells need not include the RB and LB loci. As discussed above, monocot cells (as well as dicot cells) can be transformed by electroporation or particle-gun bombardment methods known in the art. Other transformation-enhancing methods known in the art can also be employed.

It will be appreciated that a gene construct according to the present invention can be circular or linear, depending upon the method used to introduce the construct into target cells. For example, use of *A. tumefaciens* T-DNA requires that the construct be circular (i.e., RB is coupled to LB). With other transformation techniques such as electroporation, a circular construct is not required.

EXAMPLES 1–4

Figure 3:
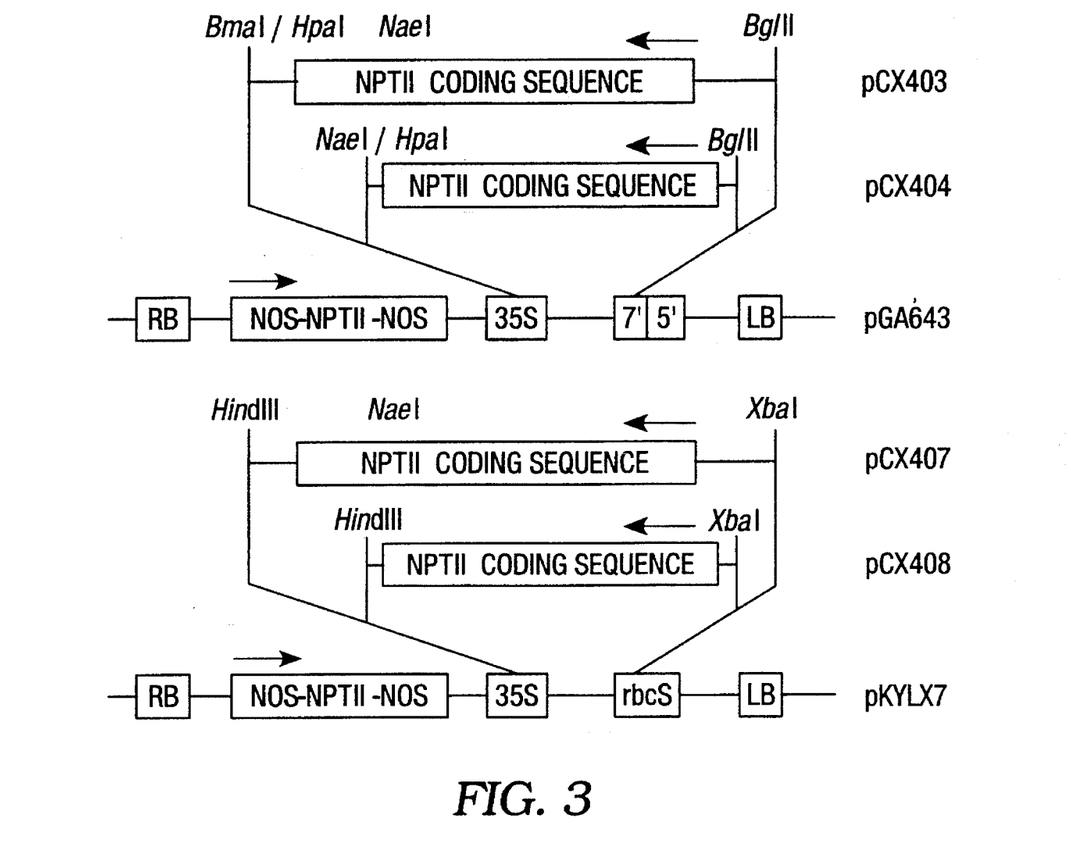
FIG. 3 shows genetic maps of the genetic constructs of in Examples 1–4.

Four antisense gene constructs according to the present invention were prepared against the NPTII gene using the transposon Tn5 coding sequence (FIG. 3). NPTII is a completely celiable positively selectable marker gene that is widely used in transformation of plant cells.

In FIG. 3, RB and LB designate right and left T-DNA borders; Nos-NPTII-Nos designates the neomycin phosphotransferase gene controlled by the promoter (Nos on the left) and terminator (Nos on the right) of the nopaline synthase gene; 35S is the 35S promoter from cauliflower mosaic virus; and rbcS is the polyadenylation signal of the rubisco ss gene. Arrows indicate the orientation of the respective genes.

To construct the anti-NPTII genes, a 1000 base-pair (bp) SmaI-BglII fragment and 650 bp NaeI-BqlII fragments of Tn5, both including a 35 bp untranslated region and translation start codon, were isolated from pGA342. To construct pCX403 and pCx404, these fragments were directly cloned into the *Agrobacterium tumefaciens* expression binary vector pGA643 at HpaI and BglII sites so that the Tn5 coding sequence was in the inverted orientation and under the control of the CaMV 35S promoter. In order to insert the Tn5 coding sequence into the binary vector pKYLX7 (Schardl et al., *Gene* 61:1–11 (1987)) in the inverted orientation to create pCX407 and pCX408, the SmaI-BqlII and NaeI-BglII fragments were first cloned into pBluescript II KS- plasmids at BamHI and EcoRV sites. The Tn5 coding sequence was then resolvable as HindIII-XbaI fragments which were directly inserted into the pKYLX7 expression cassette in the inverted orientation. These constructs were introduced into *Agrobacterium tumefaciens* strains EHA105 and LBA4404 via freeze-thaw direct transformation, Offringa et al., *EMBO J.* 9:3077–3084 (1991); An et al., in *Plant Molecular Biology Manual* A3, pp. 1–19 (Kluwer Academic Publishers, 1988), and their intactness was confirmed by restriction analysis.

Tobacco leaf discs were infected with the transformed *A. tumefaciens* bacteria to permit biological assay of anti-NPTII gene function. After cocultivation of the leaf discs with the transformed *A. tumefaciens,* the leaf discs were incubated on MS shooting medium, as known in the art, containing various concentrations of kanamycin: 0, 50, 100, 200, and 400 mg/L.

This assay demonstrated that a gene construct comprising the NPTII gene as a PSM and an anti-NPTII locus functioned as a positive/negative selectable marker. This assay also permitted a determination of the appropriate kanamycin concentration required for negative selection by comparing to positive control transformations of leaf discs using the pGA643 binary vector. This assay also exemplifies methods that would be used or adapted by persons skilled in the art to construct any of a wide variety of gene constructs according to the present invention.

The results are assembled in Table 1, showing the number of calli that emerged per leaf disc on MS medium containing various kanamycin concentrations by the different gene constructs. In Table 1, entries marked "+++" indicate that calli formed all around the cut edges of the leaf discs (more than 20 calli per leaf disc). Numerical values represent the average of two similar experiments. Each experiment employed three replica plates for each concentration of kanamycin, with four leaf discs per plate. Plates were incubated at 22° C. under a photoperiod of 16 hours light and 8 hours darkness. Initiation of callus development was seen about two weeks after co-cultivation. The number of calli that emerged from each leaf disc were scored after about four weeks.

TABLE I

| Example | Construct | Kanamycin Concentration (mg/L) | | | | |
|---------|-----------|---|----|-----|-----|-----|
|         |           | 0 | 50 | 100 | 200 | 400 |
| *       | pGA643    | +++ | +++ | +++ | +++ | +++ |
| 1       | pCX403    | +++ | 4.50 | 2.45 | 0.00 | 0.00 |
| 2       | pCX404    | +++ | 4.50 | 2.45 | 0.00 | 0.00 |
| 3       | pCX404    | +++ | 4.51 | 2.55 | 0.00 | 0.00 |
| 4       | pCX407    | +++ | 4.20 | 2.15 | 0.00 | 0.00 |
| **      | Control   | +++ | 0.00 | 0.00 | 0.00 | 0.00 |

* pGA643 served as the positive control.
** The negative control lacked any gene constructs.

Table 1 illustrates that the anti-NPTII genes are completely effective as negative-selection markers with clear utility for gene targeting according to the present invention. A kanamycin concentration of 200 mg/L, which is commonly used in plant transformations, will completely suppress callusing and shoot formation using the anti-sense RNA constructs. Concentrations lower than 200 mg/L did not completely inhibit callusing or shoot formation. This may indicate that the kanamycin-sensitivity phenotype generated by the construct is concentration-dependent. Nevertheless, the results of Table 1 demonstrate that the kanamycin-resistance phenotype is overcome by anti-sense RNA when sufficient antibiotic is supplied to the selection medium.

The following are outlines of experimental protocols that can be readily followed or modified by persons skilled in the art for transforming a wide variety of cells using gene constructs according to the present invention.

Figure 4:
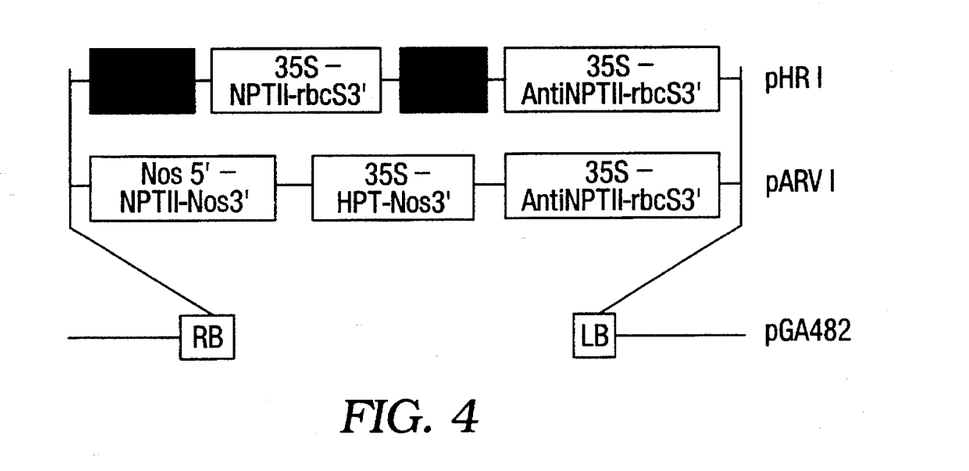
FIG. 4 shows genetic maps of alternative embodiments of constructs according to the present invention particularly suitable for transforming plant cells.

Another representative construct according to the present invention is the pARV1 construct shown in FIG. 4. (In FIG. 4, RB and LB designate the right and left T-DNA borders; Nos5' and Nos3' designate the promoter and terminator, respectively, of the nopaline synthase gene; NPTII designates the neomycin phosphotransferase gene, a representative PSM locus; rbcS3' designates the polyadenyiation signal of the rubisco ss gene; HPT designates the hygromycin phosphotransferase gene, a representative GOI; and Anti-NPTII designates the antisense-NPTII gene.) The pARV-I construct is constructed by placing the hygromycin resistance cassette adjacent the NPTII gene. The anti-NPTII locus is driven by the 35S promoter. Essentially, the hygromycin resistance cassette (35S-HPT-Nos3') is subcloned into pCX408. The resulting construct (pARV-1) is usable, for example, to transform dicotyledonous leaf discs (such as tobacco) using conventional procedures as described above. *A. tumefaciens* strains EHA105 and LBA4404 harboring the pARV-I construct can be used to deliver the construct into the target plant cells. The binary vector pGA643 can be used as a positive control in assays of construct function in homologously recombinant transformed cells. Suitable negative controls are leaf discs co-cultured without gene constructs. The procedure for delivering the construct into *A. tumefaciens* cells is preferably the freeze-thaw technique as described above. After co-cultivation of the bacteria with the target cells, the *A. tumefaciens* bacteria are washed from the leaf discs. The discs are subsequently cultured on MS callusing and shoot-producing media containing hygromycin. Hygromycin-resistant calli that arise (developed from homologously recombinant target cells in the leaf discs) can be further subcultured to produce sectors suitable for plantlet regeneration. Regenerated plants are usable as plant-cell sources for Southern and Northern blot analysis of the homologously recombinant constituent cells. The Southern blots are probed with pCX408 and pARV-I to determine copy number of the NPTII sense and antisense genes as well as the hygromycin-resistance gene (GOI). The Northern blots of these cells can be probed determine level of expression of the sense and antisense NPTII loci. NPTII assays can also be employed to demonstrate translation of the "sense" NPTII locus. Plant tissue harboring both sense and antisense NPTII loci can be placed on kanamycin to confirm sensitivity or resistance to the antibiotic. Thus, the Anti-NPTII inhibition of co-introduced sense NPTII loci in plants harboring both loci can be verified.

Another example of a GOI, not intended to be limiting, is the acyl carrier protein (ACP-I) from Arabidopsis. Acyl carrier protein is a cosubstrate and cofactor in de novo lipid synthesis in plants. The NPTII gene, as an example of a suitable PSM, is inserted between two genomic sequences flanking the ACP-I gene in Arabidopsis. This is possible because we have cloned the ACP-I gene and have subclones that lack the coding sequence but have flanking sequences. The NPTII gene is also inserted between the flanking sequences. The antisense NPTII gene is placed immediately outside the ACP-I flanking regions to create pHRI, shown in FIG. 4. (In FIG. 4, the dark regions designate arabsopsis ACP-I homologous flanking sequences.)

Subsequent co-cultivation of target cells with Agrobacteria containing the pHRI construct is followed by selection on kanamycin-containing medium. Calli resistant to the antibiotic are subcultured to regenerate plants from surviving homologously recombinant cells. Southern-blot analysis can be performed on selected transformants (not the entire population of target cells!) by probing with intact ACP-I gene. Any band shifts seen on the blots with individual transformants demonstrate that the selection procedure has disrupted the genomic target allele via homologous recombination. Such fragments can be gel-purified using conventional techniques. Polymerase chain reaction (PCR) methods can also be used to verify the disruption. (For PCR, the-sense NPTII gene is used as the template.)

Having illustrated and described the principles of our invention in several preferred embodiments, examples, and variations thereof, it should be apparent to those skilled in the art that the present invention may be modified in arrangement and detail without departing from said principles. We claim as our invention all modifications coming within the scope and spirit of the following claims.

We claim:

1. A polynucleotide construct adapted to integrate into a target polynucleotide by recombination, the construct comprising:
    (a) a first and second nucleotide sequence each homologous with a corresponding nucleotide sequence flanking a desired integration site in a target polynucleotide, said first and second nucleotide sequences being capable of undergoing homologous recombination with said corresponding nucleotide sequence flanking the desired integration site;
    (b) a third nucleotide sequence operably linked to said first and second nucleotide sequences, said third nucleotide sequence coding for a promoter and a positive selectable marker via transcription initiated at said promoter, and said third nucleotide sequence being situated in a region of said construct located between said first and second nucleotide sequences so as to enable said third nucleotide sequence to become integrated into said target polynucleotide whenever said polynucleotide construct homologously recombines with said target polynucleotide; and
    (c) a fourth nucleotide sequence operably linked to said first, second, and third nucleotide sequences, said fourth nucleotide sequence coding for a promoter that is stronger than said promoter of said third nucleotide sequence, and an antisense transcript to said positive selectable marker, and said fourth nucleotide sequence being situated outside said region located between said first and second nucleotide sequences.

2. The polynucleotide construct of claim 1 adapted to integrate into a genome of a cultured plant cell.

3. A cultured plant cell comprising the polynucleotide construct of claim 1.

4. The polynucleotide construct of claim 1 wherein said positive selectable marker codes for an antibiotic resistance factor.

5. The polynucleotide construct of claim 1 further comprising a gene of interest linked to said first, second, third, and fourth nucleotide sequences, wherein said gene of interest is situated in said region located between said first and second nucleotide sequences.

6. A target polynucleotide having undergone homologous recombination with the polynucleotide construct of claim 1 so as to incorporate said positive selectable marker into said target polynucleotide.

7. A vector derived from *Agrobacterium tumefaciens* comprising the polynucleotide construct of claim 1.

8. The vector of claim 7, capable of transforming plant cells in culture susceptible to infection by *Agrobacterium tumefaciens*.

9. An *Agrobacterium tumefaciens* cell comprising the vector of claim 7.

10. A cultured plant cell comprising the target polynucleotide of claim 6.

11. The polynucleotide construct of claim 2 further comprising a gene of interest situated adjacent said positive selectable marker in said region between said first and second nucleotide sequences.

12. The polynucleotide construct of claim 2 wherein said positive selectable marker codes for an antibiotic resistance factor.

13. A cultured plant cell comprising the polynucleotide construct of claim 2.

14. The polynucleotide construct of claim 2 that has incorporated by recombination at said target site in said target genome said region situated between said first and second nucleotide sequences, said region including said positive selectable marker.

15. The polynucleotide construct of claim 14 that has incorporated by recombination at said target site in said target genome of a target cell said region situated between said first and second nucleotide sequences.

16. A vector derived from *Agrobacterium tumefaciens* comprising the polynucleotide construct of claim 2.

17. An *Agrobacterium tumefasciens* cell comprising the vector of claim 16.

18. A method for the positive selection of cultured plant cells that have undergone homologous recombination between the genome of said plant cells and a polynucleotide construct, said polynucleotide construct comprising:

(i) a first and a second nucleotide sequence each homologous to a corresponding nucleotide sequence flanking a desired integration site in the genome of said plant cells at which said first and second nucleotide sequences can homologously recombine with said integration site in the genome of said plant cells;

(ii) a third nucleotide sequence operably linked to and flanked by said first and second nucleotide sequences, said third nucleotide coding for a promoter and a positive selectable marker; and (iii) a fourth nucleotide sequence operably linked to said first and second nucleotide sequences but not linked between said first and second nucleotide sequences, said fourth nucleotide sequence coding for a second promotor that is stronger than said first promoter and an antisense transcript that is capable of blocking expression in said plant cells of said positive selectable marker;

said method comprising:

(a) transforming said plant cells with said polynucleotide construct and allowing for said polynucleotide construct to integrate with the genome of said plant cells;

(b) culturing said plant cells in the presence of a positive selection agent and killing said transformed cells that have undergone non-homologous via exposure of said transformed cells to said positive selection agent and expression of said fourth nucleotide sequence of said polynucleotide construct that expresses in said transformed plant cells that have undergone non-homologous recombination an antisense transcript that inhibits expression of said selectable marker; and (c) isolating said transformed plant cells that have undergone homologous recombination and survived exposure to said positive selection agent via expression of said selectable marker of said polynucleotide construct.

19. The method of claim 18 wherein said positive selection agent is an antibiotic.

20. The method of claim 18 wherein said third nucleotide sequence further codes for a gene of interest.

21. The method of claim 20 wherein said positive selection agent is an antibiotic.

* * * * *

UNITED STATES PATENT AND TRADEMARK OFFICE
CERTIFICATE OF CORRECTION

PATENT NO. : 5,527,674
DATED : June 18, 1996
INVENTOR(S) : GUERRA ET AL.

It is certified that error appears in the above-identified patent and that said Letters Patent is hereby corrected as shown below:

On the Cover Page:

Item [56], References Cited, Other Publications, the following reference should be inserted:

Izant and Weintraub, "Constitutive and Conditional Suppression of Exogenous and Endogenous Genes by Anti-Sense RNA," *Science* *229*:345-352 (1985).

Page 1, first column, Item [56], References Cited, Other Publications,

Mizuno et al., "Unique Mechanism Regulating Gene Expression: Translational Inhibition by a Complementary RNA Transcript (micRNA)," *Proc. Natl. Acad. Sci. USA 81*:1966-1970 (1984).

should be

Mizuno et al., "A Unique Mechanism Regulating Gene Expression: Translational Inhibition by a Complementary RNA Transcript (micRNA)," *Proc. Natl. Acad. Sci. USA 81*:1966-1970 (1984).

Page 1, first column, Item [56], References Cited, Other Publications,

Izant and Weintraub, "Inhibition of Thymidine Kinase Gene Expression by Anti-Sense RNA: A Molecular Approach to Genetic analysis," *Cell 36*:1007-1015 (1984).

should be

Izant and Weintraub, "Inhibition of Thymidine Kinase Gene Expression by Anti-Sense RNA: A Molecular Approach to Genetic Analysis," *Cell 36*:1007-1015 (1984).

UNITED STATES PATENT AND TRADEMARK OFFICE
CERTIFICATE OF CORRECTION

PATENT NO. : 5,527,674
DATED : June 18, 1996
INVENTOR(S) : GUERRA ET AL.

It is certified that error appears in the above-identified patent and that said Letters Patent is hereby corrected as shown below:

Page 1, second column, Item [56], References Cited, Other Publications,

Thomas and Capecchi, "Site-Directed Mutagensis by Gene Targeting in Mouse Embryo-Derived Stem Cells," *Cell 51*:503-512 (1987).

should be

Thomas and Capecchi, "Site-Directed Mutagenesis by Gene Targeting in Mouse Embryo-Derived Stem Cells," *Cell 51*:503-512 (1987).

Page 1, second column, Item [56], References Cited, Other Publications,

DeLozanne and Spudich, "Disruption of the *Dictyostelium myosin* Heavy Chain Gene by homologous Recombination," *Science 236*:1086-1091 (1987).

should be

DeLozanne and Spudich, "Disruption of the *Dictyostelium Myosin* Heavy Chain Gene by Homologous Recombination," *Science 236*:1086-1091 (1987).

Page 2, first column, Item [56], References Cited, Other Publications,

Gal et al., "Genomic Homologous Recombination in Planta," *Embo J. 10*:1571-1578 (1991).

should be

Gal et al., "Genomic Homologous Recombination *in Planta*," *EMBO J. 10*:1571-1578 (1991).

UNITED STATES PATENT AND TRADEMARK OFFICE
CERTIFICATE OF CORRECTION

PATENT NO. : 5,527,674
DATED : June 18, 1996
INVENTOR(S) : GUERRA ET AL.

It is certified that error appears in the above-identified patent and that said Letters Patent is hereby corrected as shown below:

Page 2, first column, Item [56], References Cited, Other Publications,

> Wong and Capecchi, "Homologous Recombination Between Coinjected DNa Sequences Peaks in Early to Mid-S Phase," *Molec. Cell. Biol.* 7:2294-2295 (1987).

should be

> Wong and Capecchi, "Homologous Recombination Between Coinjected DNA Sequences Peaks in Early to Mid-S Phase," *Molec. Cell. Biol.* 7:2294-2295 (1987).

Column 2, lines 9-10, "*Proc. Natl. Acad. Sci*" should be --*Proc. Natl. Acad. Sci.*--.

Column 2, lines 12-13, "*Proc, Natl. Acad. Sci.*" should be --*Proc. Natl. Acad. Sci.*--.

Column 2, line 13, "simultaneous" should be --Simultaneous--.

Column 2, line 20, "*Crit. Rev. in Biochem. and Molec, Biol.*" should be --*Crit. Rev. in Biochem. and Molec. Biol.*--.

Column 2, lines 21-22, "*BioTechniques* 958-976" should be --*BioTechniques* 6:958-976--.

Column 2, lines 26-27, "*Proc. Natl. Acad. Sci,*" should be --*Proc. Natl. Acad. Sci.*--.

Column 3, lines 38-39, "S-subunit" should be --$\beta$-subunit--.

Column 3, lines 46-47, "*Proc, Natl. Acad. Sci.*" should be --*Proc. Natl. Acad. Sci.*--.

UNITED STATES PATENT AND TRADEMARK OFFICE
CERTIFICATE OF CORRECTION

PATENT NO. : 5,527,674
DATED : June 18, 1996
INVENTOR(S) : GUERRA ET AL.

It is certified that error appears in the above-identified patent and that said Letters Patent is hereby corrected as shown below:

Column 3, line 50, "*Mol. Gen. Genet. 4*:294-296" should be --*Mol. Gen. Genet. 224*:294-296--.

Column 8, line 9, "hopaline" should be --nopaline--.

Column 8, line 15, "PAL" should be --<u>PAL</u>--.

Column 8, line 60, "Agrobacterium" should be --*Agrobacterium*--.

Column 10, lines 57-58, "incorporated-the" should be --incorporated the--.

Column 11, lines 62-63, "Agrobacterium" should be --*Agrobacterium*--.

Column 12, line 40, "7'5 'terminator" should be --7'5' terminator--.

Column 12, line 40, "Agrobacterium" should be --*Agrobacterium*--.

Column 13, line 11, "celiable" should be --reliable--.

Column 13, line 22, "SmaI-BglII" should be --*Sma*I-*Bgl*II--.

Column 13, line 22, "NaeI-BqlII" should be --*Nae*I-*Bgl*II--.

Column 13, line 27, "HpaI" should be --*Hpa*I--.

Column 13, line 27, "BglII" should be --*Bgl*II--.

Column 13, line 32, "SmaI-BqlII" should be --*Sma*I-*Bgl*II--.

UNITED STATES PATENT AND TRADEMARK OFFICE
CERTIFICATE OF CORRECTION

PATENT NO. : 5,527,674
DATED : June 18, 1996
INVENTOR(S) : GUERRA ET AL.

It is certified that error appears in the above-identified patent and that said Letters Patent is hereby corrected as shown below:

Column 13, line 32, "NaeI-BglII" should be --*Nae*I-*Bgl*II--.

Column 13, line 34, "BamHI" should be --*Bam*HI--.

Column 13, line 34, "EcoRV" should be --*Eco*RV--.

Column 13, line 35, "HindIII-XbaI" should be --*Hin*dIII-*Xba*I--.

Column 14, line 47, "polyadenyiation" should be --polyadenylation--.

Column 15, lines 21 and 25, "Arabidopsis" should be --*Arabidopsis*--.

Column 15, lines 33-34, "Agrobacteria" should be --*Agrobacteria*--.

Signed and Sealed this

Twenty-sixth Day of May, 1998

*Attest:*

BRUCE LEHMAN

*Attesting Officer*         *Commissioner of Patents and Trademarks*